(12) United States Patent
Dorf

(10) Patent No.: US 6,514,505 B2
(45) Date of Patent: Feb. 4, 2003

(54) COSMETIC COMPOSITION FOR ADDING FULLNESS TO THE LIPS AND SURROUNDING AREA

(76) Inventor: Paula Dorf, 205 W. End Ave., Ste, 9J, New York, NY (US) 10023

( * ) Notice: Subject to any disclaimer, the term of this patent is extended or adjusted under 35 U.S.C. 154(b) by 0 days.

(21) Appl. No.: 09/755,307

(22) Filed: Dec. 28, 2000

(65) Prior Publication Data

US 2002/0085982 A1 Jul. 4, 2002

(51) Int. Cl.[7] ............................. A61K 6/00; A61K 7/00; A61K 7/025
(52) U.S. Cl. .......................................... 424/401; 424/64
(58) Field of Search .................................... 424/401, 64

(56) References Cited

U.S. PATENT DOCUMENTS 5,505,937 A * 4/1996 Castrogiovanni et al. ..... 424/64
6,080,390 A * 6/2000 Calello et al. ................ 424/64

* cited by examiner

Primary Examiner—Thurman K. Page
Assistant Examiner—S. Howard
(74) Attorney, Agent, or Firm—Ward & Olivo

(57) ABSTRACT

A cosmetic composition is provided that is particularly intended for application to areas constituting or surrounding the lips. It is a silicone-based formula, preferably comprising a solvent, masking oil, moisturizer, skin protectant, pigment, wax and antioxidant, specifically designed to enhance the fullness of the lips and their surrounding area which decrease as a result of the aging process. In addition, the cosmetic may be used to fill in wrinkles, cracks and/or crevices that surround the lip area which are also a result of the aging process. The invention is a creamy formula which easily fills such lines, resulting in a smooth texture of any areas to which it is applied. The effect is a reduction in the ability of facial lines to cause the undesirable bleeding of lipstick into areas of the face other than the lips.

20 Claims, No Drawings

COSMETIC COMPOSITION FOR ADDING FULLNESS TO THE LIPS AND SURROUNDING AREA

TECHNICAL FIELD OF THE INVENTION

The present invention relates to a composition of a cosmetic for application to the lips and surrounding skin area. More specifically, the invention relates to a composition intended for topical deposit into the fine facial lines that form on and around the lips during the aging process. With use of the product, such lines are "filled in", thereby enhancing the fullness of the appearance of the lips, providing a smoother appearance of the lips and making it impossible for any lipstick or other version thereof to mistakenly gather therein and cause an undesirable appearance.

BACKGROUND OF THE INVENTION

Facial lines and wrinkles are particularly noticeable and occur most frequently around the lip area. Reduction of, or at least covering, the appearance of facial lines and/or wrinkles is an important function of a cosmetic skin composition. The present invention is a composition for a cosmetic for application to skin surfaces, such as the facial lines on or around the lip area.

Traditionally, wearers of lipstick and other colored lip products have encountered difficulty with fine facial lines that commonly form around the lips. These facial lines often cause lipstick to "bleed" into them. Bleeding, in terms of lipstick usage, refers to the spreading of makeup from its desired location into fine facial lines. When bleeding occurs, the lipstick will settle into lines and emphasize their existence by depositing color in the crevices.

Thus far, a suitable manner by which bleeding can be prevented has not been found. Use of colored lipliner pencil or pen to aid in the maintenance of lipstick on the lips can be somewhat effective, but it still does not fully prevent the bleeding. Traditional lipliner only aims to prevent the bleeding of lipstick by forming a barrier around the lips. However, lipliner is easily worn off and the lipstick can subsequently bleed into untreated facial lines.

The appearance of fine facial lines and wrinkles is a serious concern for many during the aging process. While most people would prefer that such lines and wrinkles be completely eliminated, this is impractical. However, steps can be taken to reduce their prominence on the face.

There are many lip-care and lip-beautification products available to suit different needs of a wide variety of users. Some lipliners, such as that disclosed in U.S. Pat. No. 5,352,441, are powder-based and are applied with a water-wetted brush. This cosmetic serves a beautification purpose as well as a functional one. The product provides a lip line for beautification purposes and the lip line also helps prevent "bleeding" or "feathering" of lipstick into the lipliner.

Other lipliners are in the form of a waxy pencil which deposit color on the lips in hopes of maximizing the length and the intensity of the lip color.

Still other lipliners, such as that disclosed in U.S. Pat. No. 5,747,017, are available in a concentrated liquid form that dries after application to the lips. The product forms a clear film over the lips so that the lip color lasts longer than normal lipstick. The product is merely a lip beautification cosmetic relied on as an alternative to lipstick. The lipliner only colors the lips and offers a longer staying power due to its water insolubility.

These forms of lipliners do not aim to take preventative measures with regard to fine lines and wrinkles on or surrounding the lips, which is the focus of the current invention. Thus far, there has been no product that has been intended for application to the upper lip region for the purpose of filling in lines and ridges to prevent the bleeding of lipstick into them. Although previous designs have had the purpose of preventing lip color from smearing off of the lips or losing intensity, none have specifically been designed to eliminate the likelihood of bleeding into facial lines by smoothing over the crevices.

The invention described herein solves the problem, among others, of overcoming the loss of fullness in the lips and their surrounding area due to aging. In addition, the invention solves the problem of lipstick or other lip coloring bleeding or feathering into facial lines. In general, the invention fills in any crevices, cracks, or wrinkles that may be caused as a result of the aging process, thereby providing a smooth and more full (or plump) appearance. The smooth formula ensures that every line is properly filled so that any lipstick applied to the lips will not have the opportunity to seep into surrounding cracks in the skin.

SUMMARY OF THE INVENTION

The present invention provides a novel means for "filling in" facial lines. In particular, the invention is for a creamy cosmetic composition that can deposit colorless material into facial lines to provide a smooth surface, thereby hiding or covering any undesirable lines. In addition, when used on the lips, the invention prevents lipstick or other colored lip product from seeping into cracks or lines thereon. In addition, the cosmetic composition may contain chemicals designed to soften and smooth the skin in order to minimize the appearance of facial lines, as well as prevent additional lines from forming.

In light of the above described disadvantages and insufficiencies of the prior art, it is an object of the invention herein to provide a cosmetic composition for application to the lips and/or surrounding skin area to fill in superficial cracks, crevices, and wrinkles to add fullness and smoothness to the appearance of the lips and/or other skin area.

It is another object of the invention to provide a cosmetic composition for application to the lips and/or surrounding skin area such that the application of lipstick or other lip makeup may be smooth, seamless, and long-lasting.

Yet another object of the invention is to provide a product of clear or transparent composition.

Still another object of the invention is to provide a product that is appropriate for use around the mouth.

Yet another object of the invention is to provide a product that imparts a desirable feel on the skin.

Yet another object of the invention is to provide a product that is sufficiently thick to prevent the product from bleeding once placed upon the skin.

Yet another object of the invention is to provide a product that requires only one smooth application stroke to ensure proper application of the material being applied, unlike traditional versions of the invention which require multiple strokes.

Yet another object of the invention is to provide a product that is more comfortable to use because of its ability to accomplish the intended task with one stroke using the present invention and because of the invention's unusually soft bristles.

Yet another object of the invention is to provide a product that is multi-purpose and may be used for eyeliner, eye shadow, and other cosmetics.

Other objects, features, and characteristics of the present invention, as well as the methods of operation and functions of the related elements of the structure, and the combination of parts and economies of manufacture, will become more apparent upon consideration of the following detailed description with reference to the accompanying drawings, all of which form a part of this specification.

DETAILED DESCRIPTION OF THE PREFERRED EMBODIMENT

As required, a detailed illustrative embodiment of the present invention is disclosed herein. However, techniques, systems and operating structures in accordance with the present invention may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein which define the scope of the present invention. The following presents a detailed description of a preferred embodiment of the present invention, as well as some alternate embodiments of the present invention.

As discussed above, the present invention relates generally to a product to diminish the effect of facial lines and wrinkles, especially for the areas on or surrounding the lips.

A preferred embodiment of the present invention comprises a composition made from cyclomethicone, paraffin wax, polybutene, dioctyl malate, c30-45 alkyl methicone, mica, pershea butter, aloe vera extract, vitamin A, PEG-8 and tocopherol and ascrbyl palmitate, ascorbic acid and citric acid and propyl paraben.

The present invention utilizes cyclomethicone as a solvent. This volatile silicone base provides the smooth feel to the user's skin during its application. The invention further comprises vitamin A as an anti-aging compound essential for the growth and function of healthy skin cells. The vitamin A serves as an antioxidant for the skin, thereby keeping the user's skin young looking and vibrant.

The chemical composition of the present invention allows for smooth application to the skin around the mouth. The composition is viscous when applied to the facial area and deposits a transparent material in and around facial lines, thereby preventing other makeup from entering said facial lines and highlighting their presence. Some acceptable viscosity increasing agents which may be used with the invention include alkyl galactomannan, silica, talc, magnesium silicate, sorbitol, colloidal silicone dioxide, magnesium aluminum silicate, zinc stearate, wool wax alcohol, sorbiton, sesquioleate, cetyl hydroxy ethyl cellulose and other modified celluloses. Some suitable solvents include propylene glycol, glycerine, cyclomethicone, polyethylene glycols, hexalene glycol, diol and multi-hydroxy based solvents. Suitable vitamins include A, D-3, E, B-5 and E acetate.

In an alternative embodiment of the invention, the composition also comprises a masking oil. Suitable masking oils include, for example, polydecene, polybutene, PPG-14 butyl ether, non-volatile silicones, isopropyl myristate, isopropyl palmitate, $C_{12}$–$C_{15}$ alkyl benzoates, and mineral oils.

The components used in the composition comprise a skin protectant which moisturizes and softens skin, thereby reducing the visibility of said facial lines. The present invention therefore allows a smooth application of the cosmetic material to the skin. The smooth application of the invention enables a user to apply the cosmetic with a singular fluid motion. In the preferred embodiment of the invention, the skin protectant is pershea butter. In alternative embodiments, the skin protectant can be allantoin, cocoa butter, dimethicone, glycerin, petrolatum, shark liver oil, white petrolatum, and mixtures thereof.

The composition of the present invention may contain pigment to give the composition different shades of color. The preferred embodiment utilizes mica as a pigment, to give the composition one shade for application of the makeup to skin. Because different people have different skin types, and people may prefer a different shade of cosmetic to apply to their skin, different pigments may be added to different embodiments of the invention. Suitable pigments include various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof.

The compositions used in the method of the invention contain an oil to permeate and penetrate the skin, providing a moisturizer. The oils can lubricate and soften dry skin as they provide a therapeutic relaxant to tight wrinkled skin. In the preferred embodiment, the composition utilizes ascrbyl palmitate, and dioctyl malate as moisturizing oils. In alternative embodiments, several nonvolatile oils, volatile oils, and mixtures thereof can be added.

Nonvolatile oils that may be used include such esters as isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like.

In another alternative embodiment, the oil may also comprise naturally occurring glyceryl esters of fatty acids, or triglycerides. Both vegetable and animal sources may be used. Examples of such oils include castor oil, lanolin oil, triisocetyl citrate, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

In yet another alternative embodiment, synthetic or semi-synthetic glyceryl esters can be substituted for oils. For example, fatty acid mono-, di-, and triglycerides which are natural fats or oils that have been modified may be substituted for oils. These oil substitutes include acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable for use as the oil are nonvolatile hydrocarbons such as isoparaffins, hydrogenated polyisobutene, mineral oil, squalene, petrolatum, and so on.

The compositions may contain a wax to thicken the composition. The wax thickens and stiffens the composition and can possess moisturizing qualities. Alternative embodiments of the invention can include animal waxes, plant waxes, mineral waxes, silicone waxes, synthetic waxes, and petroleum waxes.

Examples of waxes that can be used include bayberry, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, ozokerite, paraffin, PEG-6 beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, synthetic wax, stearoxy dimethicone, dimethicone behenate, stearyl dimethicone, and the like, as well synthetic homo- and copolymer waxes from the ethylene series. Preferred waxes are paraffins.

Additional ingredients in the composition include antioxidants, UV absorbing compounds and other materials described herein.

The antioxidants which may be used in the formulations are butylated hydroxyanisole, butylated hydroxytoluene, tocopherol, tocopheryl acetate, ascorbyl palmitate, retinol, retinyl palmitate, hydroquinone and proanthocyanadines.

The ultra-violet absorbing compounds which may be used in the formulations are selected from the group consisting of octyl methoxycimmate, p-aminobenzoic acid, p-aminobenzoic acid esters, benzophenone-3 and other FDA approved sunscreens.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof.

What is claimed is:

1. A chemical composition for a cosmetic, wherein said composition comprises:
   paraffin wax;
   polybutene;
   dioctyl malate;
   c30-45 alkyl methicone;
   mica;
   pershea butter;
   aloe vera extract;
   vitamin A;
   PEG-8 and tocopherol and ascrbyl palmitate;
   ascorbic acid and citric acid; and propyl paraben.

2. A chemical composition according to claim 1, wherein said cosmetic composition when applied to the lips or surrounding area enhances the fullness of said lips.

3. A chemical composition according to claim 1, wherein said cosmetic composition when applied to the lips or surrounding area eliminates the visibility of facial wrinkles by filling in each crevice.

4. A chemical composition according to claim 1, wherein said composition further comprises synthetic or semi-synthetic glyceryl esters.

5. A chemical composition according to claim 4, wherein said synthetic or semi-synthetic glyceral esters are selected from the group consisting of: acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

6. A chemical composition according to claim 1, wherein said composition comprises nonvolatile hydrocarbons.

7. A chemical composition according to claim 6, wherein said nonvolatile hydrocarbons are selected from the group consisting of: isoparaffins, hydrogenated polyisobutene, mineral oil, squalene, and petrolatum.

8. A chemical composition according to claim 1, wherein said composition comprises a viscosity increasing agent selected from the group consisting of: alkyl galactomannan, silica, talc, magnesium silicate, sorbitol, colloidal silicone dioxide, magnesium aluminum silicate, zinc stearate, wool wax alcohol, sorbiton, sesqujoleate, cetyl hydroxy ethyl cellulose and mixtures thereof.

9. A chemical composition according to claim 1, wherein said composition further comprises cyclomethicone.

10. A chemical composition for a cosmetic, wherein said composition comprises:
    at least one wax;
    polybutene;
    dioctyl malate;
    at least one solvent;
    at least one pigment;
    pershea butter;
    vitamin A;
    at least one moisturizer;
    ascorbic acid and citric acid; and
    propyl paraben.

11. A chemical composition according to claim 1, wherein said composition further comprises:
    aloe vera extract; and
    PEG-8 and tocopherol.

12. A chemical composition according to claim 10, wherein said solvent is selected from the group consisting of: propylene glycol, glycerine, $c_{30-45}$ alkyl methicone, cyclomethicone, polyethylene glycols, hexalene glycol, diol and multi-hydroxy based solvents.

13. A chemical composition according to claim 10, wherein said pigment is selected from the group consisting of: azo, mica, indigoid, triphenylmethane, anthraquinone, xanthine dyes, iron oxides, ultramarines, chromium, chromium hydroxide colors, and mixtures thereof.

14. A chemical composition according to claim 10, wherein said moisturizers are selected from the group consisting of: ascrbyl palmitate, dioctyl malate, isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, oleyl alcohol, and isocetyl alcohol, naturally occurring glyceryl esters of fatty acids, or triglycerides, castor oil, lanolin oil, triisocetyl citrate, $C_{10-18}$triglycerides, caprylic/capric/triglycerides, coconut oil, corn oil, cottonseed oil, linseed oil, mink oil, olive oil, palm oil, illipe butter, rapeseed oil, soybean oil, sunflower seed oil and walnut oil.

15. A chemical composition according to claim 10, wherein said composition further comprises synthetic or semi-synthetic glyceryl esters.

16. A chemical composition according to claim 15, wherein said synthetic or semi-synthetic glyceral esters are selected from the group consisting of: acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates.

17. A chemical composition according to claim 10, wherein said composition further comprises nonvolatile hydrocarbons.

18. A chemical composition according to claim 17, wherein said nonvolatile hydrocarbons are selected from the group consisting of: isoparaffins, hydrogenated polyisobutene, mineral oil, squalene, and petrolatum.

19. A chemical composition according to claim 10, wherein said wax is selected from the group consisting of: bayberry, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, ozokerite, paraffin, PEG-6 beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, synthetic wax, stearoxy dimethicone, dimethicone behenate, stearyl dimethicone, and synthetic homo- and copolymer waxes from the ethylene series.

20. A chemical composition according to claim 10, wherein said composition further comprises a viscosity increasing agent selected from the group consisting of: alkyl galactomannan, silica, talc, magnesium silicate, sorbitol, colloidal silicone dioxide, magnesium aluminum silicate, zinc stearate, wool wax alcohol, sorbiton, sesquioleate, cetyl hydroxy ethyl cellulose and mixtures thereof.

* * * * *